US008057532B2

(12) United States Patent
Hoffman

(10) Patent No.: US 8,057,532 B2
(45) Date of Patent: Nov. 15, 2011

(54) IMPLANTABLE FRAME AND VALVE DESIGN

(75) Inventor: Grant T. Hoffman, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 350 days.

(21) Appl. No.: 12/324,199

(22) Filed: Nov. 26, 2008

(65) Prior Publication Data
US 2009/0138069 A1    May 28, 2009

Related U.S. Application Data

(60) Provisional application No. 60/990,856, filed on Nov. 28, 2007.

(51) Int. Cl.
*A61F 2/24* (2006.01)
(52) U.S. Cl. ...................................... 623/1.24; 623/2.18
(58) Field of Classification Search ............... 623/1.24, 623/1.26, 2.14, 2.17, 2.18
See application file for complete search history.

(56) References Cited

U.S. PATENT DOCUMENTS

| | | | |
|---|---|---|---|
| 3,966,401 A | 6/1976 | Hancock et al. |
| 4,675,361 A | 6/1987 | Ward, Jr. |
| 4,798,611 A | 1/1989 | Freeman, Jr. |
| 4,800,603 A | 1/1989 | Jaffe |
| 4,813,958 A | 3/1989 | Dixon |
| 4,813,964 A | 3/1989 | Dixon et al. |
| 4,861,830 A | 8/1989 | Ward, Jr. |
| 4,902,508 A | 2/1990 | Badylak et al. |
| 5,554,389 A | 9/1996 | Badylak et al. |
| 5,595,571 A | 1/1997 | Jaffe et al. |
| 5,597,378 A | 1/1997 | Jervis |
| 5,607,465 A | 3/1997 | Camilli |
| 5,720,777 A | 2/1998 | Jaffe et al. |
| 5,843,180 A | 12/1998 | Jaffe et al. |
| 5,843,181 A | 12/1998 | Jaffe et al. |
| 5,957,949 A | 9/1999 | Leonhardt et al. |
| 5,993,844 A | 11/1999 | Abraham et al. |
| 6,099,567 A | 8/2000 | Badylak et al. |
| 6,206,931 B1 | 3/2001 | Cook et al. |
| 6,245,102 B1 | 6/2001 | Jayaraman |
| 6,299,637 B1 | 10/2001 | Shaolian et al. |
| 6,409,752 B1 | 6/2002 | Boatman et al. |
| 6,485,723 B1 | 11/2002 | Badylak et al. |

(Continued)

FOREIGN PATENT DOCUMENTS

WO    WO95/31945    11/1995

(Continued)

OTHER PUBLICATIONS

U.S. Appl. No. 12/265,188, filed Nov. 5, 2008, Hoffman.

(Continued)

*Primary Examiner* — Thomas J Sweet
*Assistant Examiner* — Megan Wolf
(74) *Attorney, Agent, or Firm* — Buchanan Nipper

(57) ABSTRACT

Implantable prosthetic valves comprising support frames are provided. The support frames may include a plurality of symmetrically arrayed interconnected U-shaped member structures. Preferred support frames are tubular structures enclosing a longitudinal axis and including a plurality of U-shaped member structures facing a distal or a proximal end of the support frame. Each U-shaped member structure may be connected to a single longitudinally adjacent U-shaped member facing in an opposite longitudinal direction, as well as two laterally adjacent U-shaped members.

19 Claims, 6 Drawing Sheets

U.S. PATENT DOCUMENTS

| | | | |
|---|---|---|---|
| 6,508,833 B2 | 1/2003 | Pavcnik et al. | |
| 6,752,826 B2 | 6/2004 | Holloway et al. | |
| 6,939,377 B2 | 9/2005 | Jayaraman | |
| 7,070,616 B2 | 7/2006 | Majercak et al. | |
| 7,087,089 B2 | 8/2006 | Patel | |
| 7,261,732 B2 | 8/2007 | Justino | |
| 7,569,071 B2 * | 8/2009 | Haverkost et al. | 623/1.24 |
| 2003/0149471 A1 | 8/2003 | Briana | |
| 2003/0209835 A1 | 11/2003 | Chun et al. | |
| 2004/0180042 A1 | 9/2004 | Cook | |
| 2004/0193253 A1 | 9/2004 | Thorpe et al. | |
| 2004/0260389 A1 | 12/2004 | Case et al. | |
| 2005/0137676 A1 | 6/2005 | Richardson et al. | |
| 2005/0273159 A1 | 12/2005 | Opie | |
| 2006/0178728 A1 | 8/2006 | Camillie | |
| 2006/0210597 A1 | 9/2006 | Hiles | |
| 2007/0021826 A1 | 1/2007 | Case et al. | |
| 2007/0038291 A1 | 2/2007 | Case et al. | |
| 2007/0093887 A1 | 4/2007 | Case et al. | |
| 2007/0100435 A1 | 5/2007 | Case et al. | |
| 2007/0213813 A1 | 9/2007 | Segesser et al. | |
| 2007/0233237 A1 | 10/2007 | Krivoruchko | |
| 2007/0260327 A1 | 11/2007 | Case et al. | |
| 2008/0046071 A1 * | 2/2008 | Pavcnik | 623/1.24 |

FOREIGN PATENT DOCUMENTS

| | | |
|---|---|---|
| WO | WO03002165 | 1/2003 |
| WO | WO2007/047945 | 4/2007 |

OTHER PUBLICATIONS

Dougal et al. "Stent Design: Implications for Restenosis," Rev. Cardiovasc Med. 3 (suppl.5), S16-S229 (2002).

AAM/ISO 11135: 1994 "Medical Devices—Validation and Routine Control of Ethylene Oxide Sterilization".

PCT International Search Report for PCT/US2008/083870, Feb. 18, 2009.

PCT Written Opinion for PCT/US2008/083870, Feb. 18, 2009.

* cited by examiner

IMPLANTABLE FRAME AND VALVE DESIGN

This application claims priority to U.S. Provisional Application No. 60/990,856, filed Nov. 28, 2007, which is hereby incorporated by reference herein.

TECHNICAL FIELD

The present disclosure relates to implantable medical devices having support frames adapted for percutaneous implantation within a body vessel, as well as methods of treatment pertaining to the implantation of the medical devices.

BACKGROUND

Intraluminally implantable frames are being implanted in increasing numbers to treat a variety of conditions and are coming into greater use in a variety of fields. Frames implanted in vessels, ducts or channels of the human body can form part of a valve to regulate fluid flow within a body lumen or as scaffolding to maintain the patency of the vessel, duct or channel lumen. Implantable frames can also support a valve or valve leaflets for regulating fluid flow within a body lumen or for dilating a body lumen. One or more flexible valve leaflets can be attached to an implantable frame to form a medical device useful as an artificial valve. A variety of other implantable prostheses, such as stents, grafts and the like, also comprise an implantable frame placed within the body to improve the function of a body lumen.

The venous system includes a series of valves that function to assist the flow of blood returning to the heart. These natural valves are particularly important in the lower extremities to prevent blood from pooling in the lower legs and feet. Pooling of blood in the venous system may occur during certain situations, such as standing or sitting, when the weight of the column of blood in the vein can act to prevent positive blood flow toward the heart. This condition, commonly known as chronic venous insufficiency, is primarily found in individuals in which gradual dilation of the veins, thrombotic events, or other conditions prevent the leaflets of the native valves from closing properly. The failure of native valves to close properly can worsen, leading to significant leakage of retrograde flow such that the valve can become incompetent. Chronic venous insufficiency is a condition in which the symptoms can progress from painful edema and unsightly spider or varicose veins to skin ulcerations. Elevation of the feet and compression stocking can relieve symptoms, but do not treat the underlying disease. Untreated, the disease can impact the ability of individuals to perform in the workplace or maintain their normal lifestyle.

One promising approach to treating venous valve insufficiency includes the implantation of radially-expandable artificial valves placed using minimally-invasive techniques. Recently, the development of artificial and biological valves has been employed in an attempt to return normal pressure to the veins. These valves are generally designed to allow normal flow of blood back to the heart, while preventing retrograde flow. For example, U.S. Pat. No. 6,508,833 discloses a multiple-sided medical device comprising a closed frame of a single piece of wire or other resilient material and having a series of bends and interconnecting sides. A flexible covering of fabric or other flexible material may be attached to the frame to form an artificial valve. The flexible material utilized in these valves can comprised collagenous submucosa obtained from various animals, such as, pigs, cattle, and sheep. This material can be processed and preserved so as to be capable of inducing host tissue proliferation, remodeling, and regeneration of appropriate tissue structures, e.g., veins upon implantation in vivo (see, e.g., U.S. Pat. No. 6,485,723). The preparation of submucosal material is generally described in U.S. Pat. Nos. 4,902,508 and 5,554,389. The submucosal material can be prepared in large, flat sheets, which are subsequently cut and attached to a framing element, for example a stent, for deployment in a vein.

Dynamic fluctuations in the shape of the lumen of a body vessel, such as a vein, pose challenges to the design of implantable devices that conform to the interior shape of the body vessel. The shape of a lumen of a vein can undergo dramatic dynamic change as a result of varying blood flow velocities and volumes there through. Such dynamic change presents challenges for designing implantable intraluminal prosthetic devices that are compliant to the changing shape of the vein lumen. In addition, blood flow within a vein is intermittent and bidirectional, and subject to constant fluctuation in pressure and volume. These conditions in a vein present challenges to designing an implantable frame suitable for placement inside the vein. On one hand, an implantable frame lacking sufficient radial strength may fracture under repeated fluctuations of the vein diameter. On the other hand, an implantable frame with undesirably high levels of radial strength may lack flexibility and may damage the vein by failing to compress in response to normal fluctuations in the vein diameter. Likewise, an implantable frame with a high surface area contacting the interior wall of a vein may induce trauma in the vein wall, while an implantable frame with an insufficient surface area may lack sufficient durability. In addition, support frames are preferably configured to reduce or prevent stagnation of blood flow in regions of the body vessel proximate to the implanted frame, so as to mitigate or reduce incidence of thrombosis. Hence, what is needed is an intraluminally-placed medical device, such as an artificial valve or support frame, that is configured to withstand fluctuations in a body vessel without fracturing, to minimize the area of contact of the support frame with the wall of a body vessel and to create more desirable flow patterns around a valve within a body. For instance, a support may be configured to permit the circulation of blood or bodily fluids through a lumen and reduce the likelihood of stagnation and the potential thrombotic conditions near the support frame. These conditions, such as more turbulent flow, increased velocity of flow, larger and/or more numerous vortices, other factors, or a combination of the above, can mitigate the incidence of thrombosis formation near the implantable medical device.

There remains a need, therefore, for prosthetic valves having a support frame configured with a radial strength to maintain patency of a body vessel while supporting a means for regulating fluid within the body vessel and minimizing irritation to the body vessel after implantation.

SUMMARY

Implantable medical devices, such as prosthetic valves, comprising support frames are provided. The medical devices are preferably radially-expandable intraluminally implantable prosthetic valves including a support frame moveable from a radially expanded configuration to a radially compressed configuration. In the expanded configuration, the support frame may define a lumen extending from a proximal end to a distal end along a longitudinal axis and defining a plurality of openings in communication with the lumen.

In a first embodiment, support frames are provided. The support frames may include a first member pair connected to a second member pair by a first pair of transverse connecting members. The first member pair of circumferentially adjacent members are preferably joined at a first distal point positioned at the distal end of the support frame and at a first proximal point positioned at the proximal end of the support frame. Each member of the first pair may have a divergent portion joined to a convergent portion, with the divergent portion extending circumferentially away from the proximal point and the convergent portion extending circumferentially toward the distal point. The first pair of circumferentially adjacent members defines a first opening in the support frame, which preferably has a petal-like or diamond-like shape. The second member pair of circumferentially adjacent members may be joined at a second distal point positioned at the distal end of the support frame and at a second proximal point positioned at the proximal end of the support frame. Each member of the second member pair may have a divergent portion joined to a convergent portion, with the divergent portion extending circumferentially away from the distal point and the convergent portion extending circumferentially toward the proximal point. Alternatively, each member of the second member pair may have a divergent portion joined to a convergent portion, with the divergent portion extending circumferentially away from the proximal point and the convergent portion extending circumferentially toward the distal point. The first pair of circumferentially adjacent members may define a second opening in the support frame. Preferably, the first opening is congruent to the first opening, and is positioned across the lumen of the support frame from the first opening. The first member pair is connected to the second member pair by a first pair of transverse connecting members each extending from the divergent portion of the first member pair to a convergent portion of the second member pair. Optionally, additional pairs of transverse connecting members may connect the first member pair and the second member pair.

In a second embodiment, prosthetic valve devices are provided. The prosthetic valve preferably includes a support frame of the first embodiment and a means for regulating fluid flow in a body vessel. The prosthetic valve may be a venous valve having a flexible leaflet with a vessel-engaging portion. The one or more leaflets attached to the support frame may be formed from an extracellular matrix material or a portion of an explanted tissue valve. The second embodiment also provides delivery systems including a prosthetic valve device and device for deploying the prosthetic valve, such as a catheter. Suitable percutaneous deployment devices may include a balloon catheter having adaptations for selectively forcing a portion of the prosthetic valve against the vessel wall, and/or adaptations for radially expanding and contracting the support frame. The prosthetic valve device may be releasably attached to the deployment device by any suitable means including by the use of adhesives or removable elements such as removable sutures.

In a third embodiment, methods for treating venous insufficiency are provided, wherein the method includes deploying a support frame and/or a prosthetic venous valve such as that described above so as to force the valve body against the vascular wall, and selectively attach edges of the valve body against the vascular wall, to seat the valve within the vein. In another aspect of the third embodiment, methods for modifying blood flow in a vascular vessel are also provided.

BRIEF DESCRIPTION OF THE DRAWINGS

The following detailed description of specific embodiments of the present invention can be best understood when read in conjunction with the following drawings, where like structure is indicated with like reference numerals and in which.

DETAILED DESCRIPTION

Figure 1:
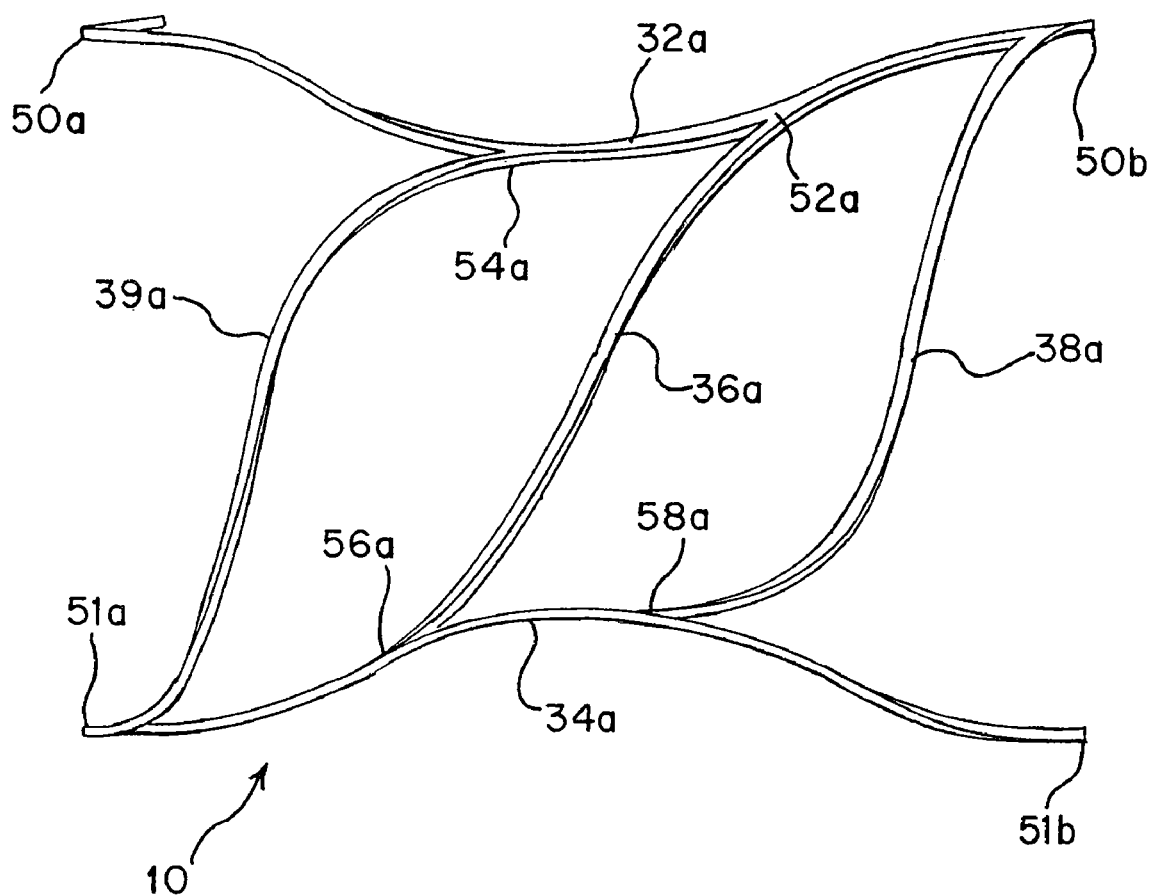
FIG. 1 is a side view of a first support frame.

For the purposes of promoting an understanding of the principles of the invention, reference will now be made to the embodiments illustrated in the drawings, and specific language will be used to describe the same.

The term "circumferential" or "circumferentially" refers to a direction or displacement measured along the exterior surface area of an assembled implantable frame in the expanded configuration that is transverse to the longitudinal axis of the implantable frame. The recitation of a first structural feature "circumferentially adjacent" to a second structural feature means that the first structural feature is the nearest first structural feature to the second structural feature when moving circumferentially along the exterior surface of an implantable frame. The term "circumferential distance" means distance measured along the exterior surface of an implantable frame in the expanded configuration.

Unless otherwise indicated, the term "longitudinal" or "longitudinally" refers to a direction measured along the longitudinal axis of the medical device, or a portion thereof such as an implantable frame. The term "longitudinally opposite" means positioned in a distal or proximal direction along the exterior surface of a medical device, such as an implantable frame, parallel to the longitudinal axis of the implantable frame. For example, the recitation of a first structural feature "longitudinally adjacent" to a second structural feature of an implantable frame means that the first structural feature is the nearest first structural feature to the second structural feature when moving longitudinally along the exterior surface of the implantable frame. Unless otherwise indicated, the term "longitudinal distance" measured between two structural features of an implantable frame means a distance or displacement measured parallel to the longitudinal axis of the implantable frame in the expanded configuration, measured along the exterior surface area of the implantable frame.

In the following discussion, the terms "proximal" and "distal" will be used to describe the opposing axial ends of the inventive sheath, as well as the axial ends of various component features. The term "proximal" is used in its conventional sense to refer to the end of the apparatus (or component thereof) that is closest to the operator during use of the apparatus. The term "distal" is used in its conventional sense to refer to the end of the apparatus (or component thereof) that is initially inserted into the patient, or that is closest to the patient.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Implantable prosthetic valves comprising support frames are provided. The support frames may provide sufficient radial strength to maintain patency of a body vessel and support a means for regulating fluid within the body vessel, such as one or more valve leaflets attached to the support frame. The support frames preferably distribute stress and strain forces caused by dynamic movement of the support frame within a body vessel. A reduced area of contact between the support frame and the body vessel wall may minimize trauma to the body vessel.

The prosthetic valve also includes a suitable means for regulating fluid through the body vessel, such as one or more valve leaflets attached to the support frame or a portion of an explanted tissue valve configured to function as the means for regulating fluid. The support frame may also be configured to provide sufficient rigidity and form to one or more attached structures. This may permit these attached structures to function as a means for regulating fluid through the body vessel. For example, a flexible biocompatible material may be configured as a valve leaflet and attached to a portion of the support frame in a manner providing sufficient shape and form to the attached material to permit the attached material to function as a valve leaflet regulating fluid flow through a body vessel.

The support frames, and prosthetic valves comprising the support frames, are preferably part of a radially-expandable implantable medical device, and may be moveable from a radially expanded configuration to a radially compressed configuration. The support frame in the expanded configuration may define a lumen extending from a proximal end to a distal end along a longitudinal axis and defining a plurality of openings in communication with the lumen. The support frame or valve in the radially compressed configuration is preferably sized and shaped for introduction to a body vessel within a catheter based delivery system, preferably using a catheter sized for placement within the human or animal vasculature. The radially expanded configuration may be sized and shaped for permanent placement within a body vessel, such as a vein, at an intended point of treatment.

Implantable Support Frame Embodiments

In a first embodiment, implantable support frames are provided. The support frames can be illustrated with respect to the following examples, which serve to illustrate certain preferred aspects of the first embodiment of the invention.

Figure 2:
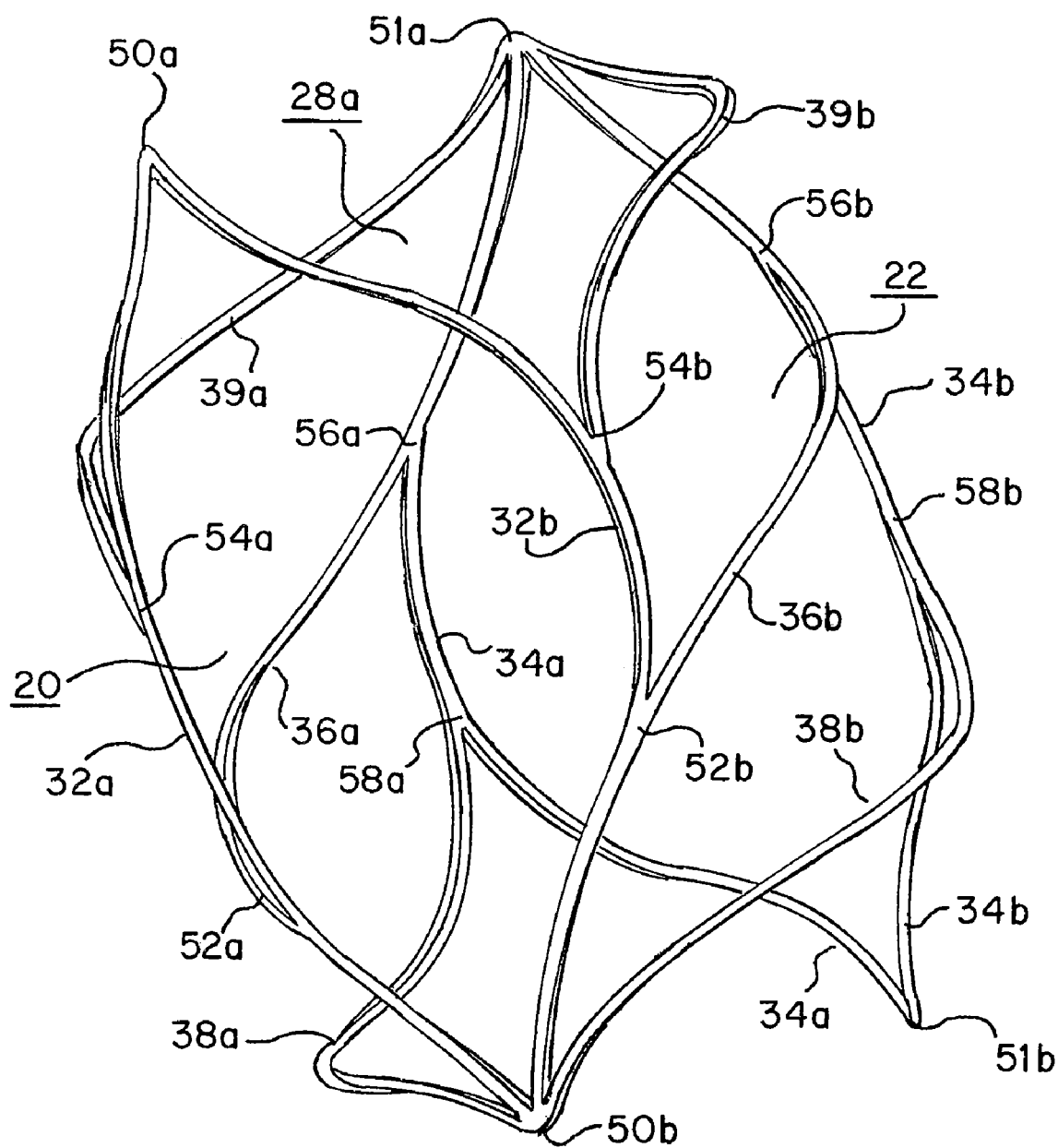
FIG. 2 is a perspective view of the first support frame.
Figure 3:
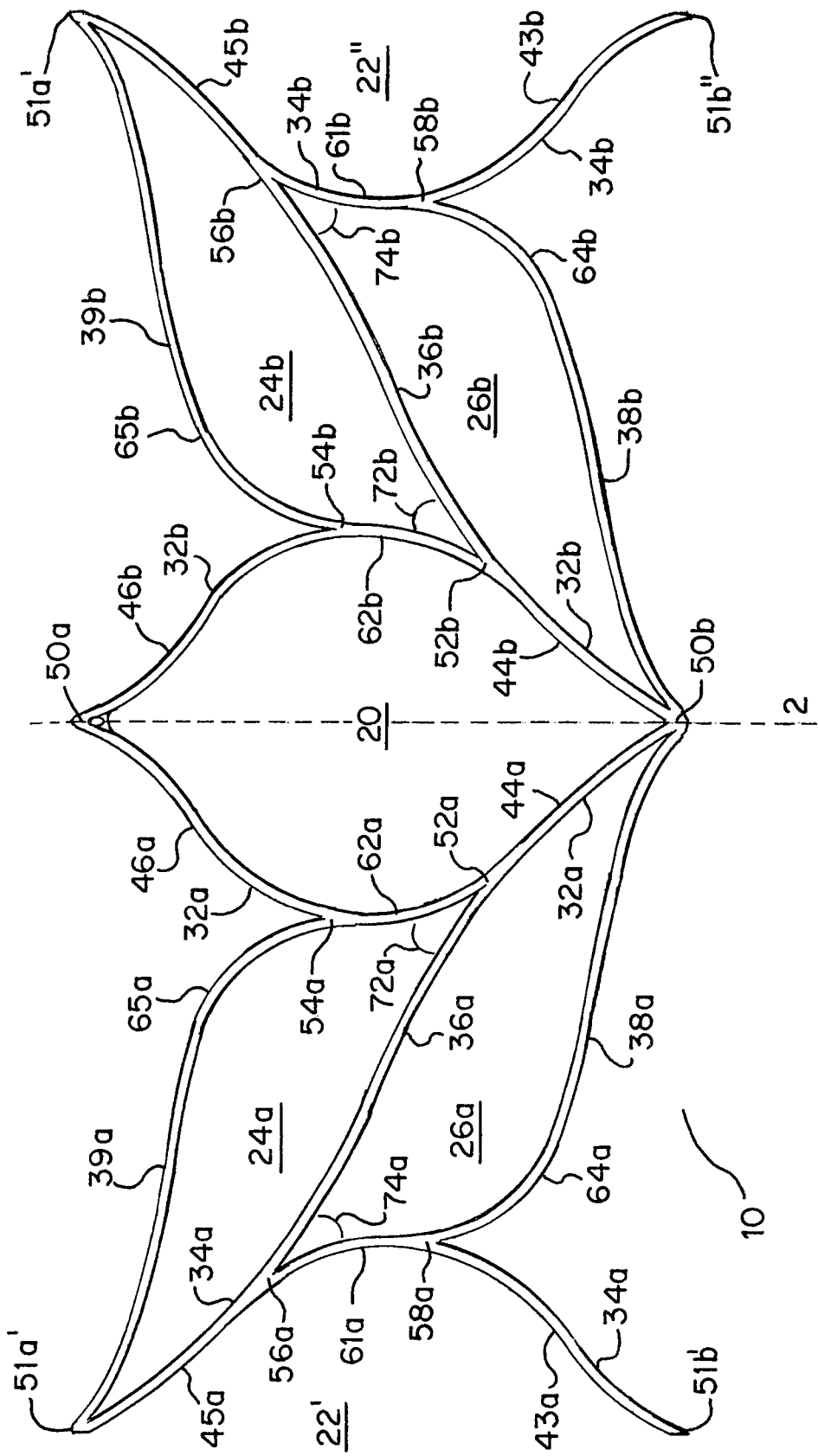
FIG. 3 is a flat plan view of the first support frame.

FIGS. 1-3 are different views of a first example of a first implantable support frame 10. FIG. 1 is a side view of the first support frame 10 including a first member 32*a* having a curvilinear profile joined to a second member 34*a* by a first transverse connecting member 36*a*. The first member 32*a* and the second member 34*a* are preferably substantially similar in shape and size, oriented in opposite longitudinal directions and aligned substantially parallel to one another. The first member 32*a* extends in a curvilinear manner from the first proximal point 50*b* to a first distal point 50*a*. Similarly, the second member 34*a* extends from the second distal point 51*a* to a second proximal point 51*b*. Optionally, the first support frame 10 may further include any number of additional transverse connecting members extending from the first member 32*a* and the second member 34*a* and longitudinally positioned proximal or distal to the first transverse connecting member 36*a*. For example, the first support frame 10 also includes a second transverse connecting member 38*a* proximal to the first transverse connecting member 36*a* and a third transverse connecting member 39*a* distal to the first transverse connecting member 36*a*. The second transverse connecting member 38*a* and the third transverse connecting member 39*a* may have a similar shape to each other that is different from the shape of the first transverse connecting member 36*a*. In the first support frame 10, the second transverse connecting member 38*a* and the third transverse connecting member 39*a* are oriented in opposite transverse directions, with the second transverse connecting member 38*a* having an inflection point 64*a* positioned closer to the second member 34*a*, while the third transverse connecting member 39*a* is positioned the inflection point 65*b* positioned closer to the first member 32*a*. The second transverse connecting member 38*a* is joined to the first member 32*a* at the first proximal point 50*b*, forming a portion of the proximal end of the first support frame 10. The third transverse connecting member 39*a* is joined to the second member 34*a* at a second distal point 51*a*, forming the distal end of the first support frame 10. The third transverse connecting member 39*a* joins the first member 32*a* at joint 54*a* and joins the second member 34*a* at the second distal point 51*a*. Similarly, the second transverse connecting member 38*a* joins the first member 32*a* at the first proximal point 50*b* and joins the second member 34*a* at joint 58*a*. The first proximal point 50*b* and the second distal point 51*a* may be substantially congruent, but oriented in opposite longitudinal directions. Similarly, joints 54*a* and 58*a* may be substantially congruent structures oriented in opposite longitudinal directions Likewise, joints 52*a* and 56*a* may be substantially congruent structures with opposing longitudinal orientation.

FIG. 2 is a perspective view of the first support frame 10. The first member 32*a* forms half of a first member pair 32*a*, 32*b* with the circumferentially adjacent second first member 32*b*. The first member pair 32*a*, 32*b* may have substantially congruent structures oriented in opposite transverse circumferential directions. The first member pair 32*a*, 32*b* may together define a first opening 20 in communication with a lumen defined by the first support frame 10. The second member 34*a* forms a second member pair 34*a*, 34*b* with the circumferentially adjacent second first member 34*b*. The second member pair 34*a*, 34*b* may have substantially congruent structures oriented in opposite transverse circumferential directions. The first member pair 34*a*, 34*b* may together define a second opening 22 in communication with a lumen defined by the first support frame 10. Preferably, the first opening 20 and the second opening 22 have at least substantially the same shape and area and are formed from congruent longitudinally adjacent member pairs (32*a*, 32*b*) and (34*a*, 34*b*) positioned across the lumen from one another. The first opening 20 and the second opening 22 may have any suitable shape, preferably including four to eight sides that are rounded or straight. For instance, the first opening 20 and the second opening 22 may have a petal-like shape as shown in the first support frame 10, or a diamond-like shape. Preferably, the first opening 20 and the second opening 22 have congruent shapes and are opposably positioned across the lumen from one another.

The first support frame 10 has a plurality of transverse connecting members (36*a*, 36*b*, 38*a*, 38*b*, 39*a*, 39*b*) connecting the first member pair 32*a*, 32*b* and the second member pair 34*a*, 34*b*. A first transverse connecting member pair 36*a*, 36*b* includes the first transverse connecting member 36*a* opposably positioned across the lumen from a second first transverse connecting member 36*b*, the transverse connecting member pair 36*a*, 36*b* each having a shape that is at least substantially similar to the first transverse connecting member 36*a*. Each member of the first member pair 32*a*, 32*b* is independently joined to a first transverse connecting pair 36*a*, 36*b* at a joint pair 52*a*, 52*b* in a "Y" shaped configuration. The opposite end of each member of the first transverse connecting pair 36a, 36b is independently joined in a "Y"-shaped configuration to the second member pair 34a, 34b at a joint pair 56a, 56b.

The first support frame 10 optionally includes a second pair of transverse connecting members 38a, 38b including the first second transverse connecting member 38a opposably positioned across the lumen from a second second transverse connecting member 38b. The second pair of transverse connecting members 38a, 38b preferably have at least substantially similar structures, and are joined at one end to the first member pair 32a, 32b at the first proximal point 50b, forming the proximal end of the first support frame 10. The opposite end of each member of the second pair of transverse connecting members 38a, 38b is independently joined in a "Y"-shaped configuration to the second member pair 34a, 34b at a joint pair 58a, 58b.

The first support frame 10 may also optionally include a third pair of transverse connecting members 39a, 39b including the first third transverse connecting member 39a opposably positioned across the lumen from a second third transverse connecting member 38b. The third pair of transverse connecting members 39a, 39b preferably have at least substantially similar structures, and are joined to the second member pair 34a, 34b at the second distal point 51a, forming a portion of the distal end of the first support frame 10. The opposite end of each member of the third pair of transverse connecting members 39a, 39b is independently joined in a "Y"-shaped configuration to the first member pair 32a, 32b at a joint pair 54a, 54b.

The plurality of transverse connecting members (36a, 36b, 38a, 38b, 39a, 39b) are preferably arranged to provide a first support frame 10 configuration having a first distal point 50a opposably positioned across the lumen from the second distal point 51a at the distal end of the first support frame 10. Similarly, the first support frame 10 may also have a first proximal point 50b opposably positioned across the lumen from a second proximal point 51b at the proximal end of the first support frame 10. Preferably, the second distal point 51a and the first proximal point 50b are substantially congruent in shape and oriented in opposite longitudinal directions. Both the second distal point 51a and the first proximal point 50b may be formed by joining either the second transverse connecting member pair 38a, 38b or the third transverse connecting member pair 39a, 39b to the first member pair 32a, 32b or the second member pair 34a, 34b, respectively. The first distal point 50a and the second proximal point 51b may be substantially congruent and oriented in opposite longitudinal directions. Preferably, the first distal point 50a is formed by joining the first member pair 32a, 32b and the second proximal point 51b is similarly formed by joining the second member pair 34a, 34b.

FIG. 3 is a flat plan view of the first support frame 10 shown in FIG. 1 and FIG. 2. The first support frame 10 may be obtained from the pattern shown in the flat plan view by cutting the pattern of FIG. 3 from either a cylindrical tube of the support frame material, or from a flat piece of the support frame material which is then rolled and joined to form the support frame by any suitable method. The tubular structure defines a lumen with a longitudinal axis 2 at the center of the lumen (e.g., as shown in FIG. 2). Upon implantation, the longitudinal axis 2 may be substantially parallel to a body vessel when the body vessel. Methods of cutting the flat plan pattern into the support frame material include laser cutting and chemical etching. Preferably, the support frames are cut from a tube or cannula of biocompatible metal (e.g., shape memory metal) to provide a radially self-expanding support frame. When forming the support frame from shape memory metal such as a nickel-titanium-containing alloy, the support frame can be laser cut from the shape memory metal. Thereafter, the support frame can be subjected to a shape-setting process in which the cut tube is expanded on a mandrel and then heated. Multiple expansion and heating cycles can be used to shape-set the support frame to the final expanded diameter. Preferably, the final expanded diameter is equal to the desired deployed diameter of the support frame. During expansion, the support frame is preferably axially restrained such that the length of the support frame does not change during expansion. The finished support frame preferably has an austenite finish temperature less than body temperature. Thus, at body temperature, the support frame will self-expand to the desired deployed diameter due to the shape memory characteristic of the metal forming the support frame.

Referring to the flat plan view of the first support frame 10 shown in FIG. 3, the first support frame 10 is symmetrical about a longitudinal axis 2. The first support frame 10 includes the first member pair 32a, 32b symmetrically disposed around the longitudinal axis 2. The first member 32a of the first member pair 32a, 32b has a bowed arcuate shape having a divergent portion 44a and a convergent portion 46a joined at an inflection point 62a. The first member 32a is joined to a congruent second first member 32b at both a first distal point 50a and at a first proximal point 50b as a first member pair 32a, 32b defining the first opening 20. The first distal point 50a and the first proximal point 50b are preferably positioned along the longitudinal axis 2. Similarly, a second first member 32b of the first member pair 32a, 32b has a bowed arcuate shape having a divergent portion 44b and a convergent portion 46b joined at an inflection point 62b.

A second member pair 34a, 34b of circumferentially adjacent members joined at a second distal point positioned at the distal end of the support frame 10 and at a second proximal point positioned at the proximal end of the support frame 10. In the flat plan view of FIG. 3, the second distal point is formed by joining points 51a' and 51a" to form a cylinder, and the second proximal point is formed by similarly joining points 51b' and 51b". This may be done by folding or the support frame pattern or by cutting the pattern into a tubular material to form the cylindrical configuration. In the cylindrical configuration, the first support frame 10 defines a second opening between the second member pair 34a, 34b. The second opening is formed by joining an opening 22' with an opening 22" shown in FIG. 3. The second member pair 34a, 34b each have a divergent portion 45a, 45b (respectively) and a convergent portion 43a, 43b (respectively) joined at an inflection point 61a, 61b (respectively).

The flat plan view of the first support frame 10 also shows three pairs of transverse connecting members (36a, 36b, 38a, 38b, 39a, 39b). The first pair of transverse connecting members 36a, 36b are joined in a "Y"-shaped configuration between the first member pair 32a, 32b and the second member pair 34a, 34b. For example, the first transverse connecting member 36a joins the first member 32a to the first second member 34a at the joint 52a and joint 56a. Preferably, the angle 72a at joint 52a between the first transverse connecting member 36a and the first member 32a is substantially congruent to the angle 74a at joint 56a between the first transverse connecting member 36a and the first second member 34a. The second first transverse connecting member 36b joins the second first member 32b to the second member 34b at the joint 52b and joint 56b. Similarly, the angles 72b and 74b are substantially congruent and are formed at joints 52b and 56b between the second first transverse connecting member 36b, the second first member 32b and the second member 34b. Each of the angles 72a, 72b, 74a and 74b are preferably acute angles, being less than 90-degrees and preferably less than about 45, 40, 35, 30, 25 or 20-degrees. The angles 72a, 72b are preferably congruent. The angles 74a, 74b are also preferably congruent to one another. Most preferably, the angles 72a, 72b, 74a, 74b are substantially congruent to one another.

The first pair of transverse connecting members 36a, 36b preferably have substantially congruent configurations and may be straight or curved. The support frame 10 may optionally include one or more additional transverse connecting pairs positioned distal and/or proximal to the first transverse connecting pair 36a, 36b. For example, a second pair of curved transverse connecting members 38a, 38b each having an inflection point 64a, 64b (respectively) are positioned proximal to the first pair of transverse connecting members 36a, 36b. A pair of fourth openings 26a, 26b are defined by the first transverse connecting members 36a, 36b, the first member pair 32a, 32b, the second transverse connecting members 38a, 38b and the second member pair 34a, 34b. The first second transverse connecting member 38a joins the first member 32a to the first second member 34a at the joint 58a and the first proximal point 50b. The second transverse connecting member 38b joins the second first member 32b to the second member 34b at the joint 58b and the first proximal point 50b.

In addition, a third pair of curved transverse connecting members 39a, 39b each having an inflection point 65a, 65b (respectively) are positioned distal to the first pair of transverse connecting members 36a, 36b. A pair of third openings 24a, 24b are defined by the first transverse connecting members 36a, 36b, the first members 32a, 32b, the third transverse connecting members 39a, 39b and the second members 34a, 34b. The first third transverse connecting member 39a joins the first member 32a to the first second member 34a at the joint 54a and the second distal point 51a. The second third transverse connecting member 39b joins the second first member 32b to the second member 34b at the joint 54b and the second distal point 51a.

Figure 4:
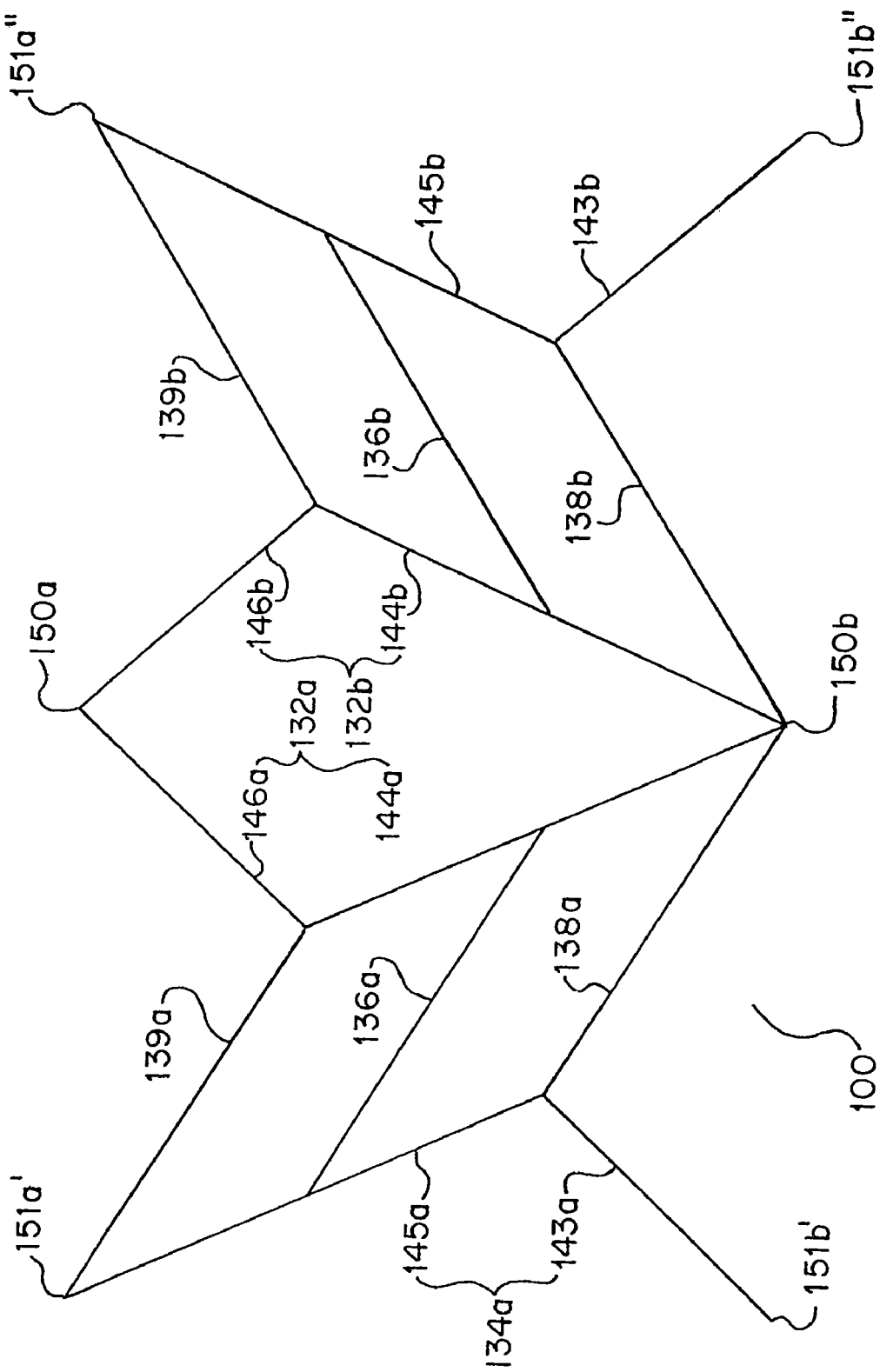
FIG. 4 is a flat plan view of a second support frame.

The members forming the support frame may be straight or curved. FIG. 4 is a flat plan view of a second exemplary support frame 100 of the first embodiment having substantially straight member pairs. The second support frame 100 is substantially similar to the first support frame 10, except as indicated below. A first member pair 132a, 132b are formed from divergent portions 144a, 144b (respectively) joined to convergent portions 146a, 146b. Unlike to first support frame 10, the first member pair 132a, 132b are each formed from straight portions. A second member pair 134a, 134b are similarly formed from divergent portions 145a, 145b and convergent portions 143a, 143b. A first pair of straight transverse connecting members 136a, 136b extend between the first member pair 132a, 132b and the second member pair 134a, 134b. The first member pair 132a, 132b and the second member pair 134a, 134b are also joined by a proximal pair of straight transverse connecting members 138a, 138b and a distal pair of straight transverse connecting members 139a, 139b. The three transverse connecting members 136a, 138a, 139a and the three transverse connecting members 136b, 138b, 139b are all substantially straight and respectively oriented substantially parallel to one another on either side of the support frame 100 (i.e., members 136a, 138a and 139a may be parallel to one another and members 136b, 138b and 139b may be parallel to one another).

Figure 5A:
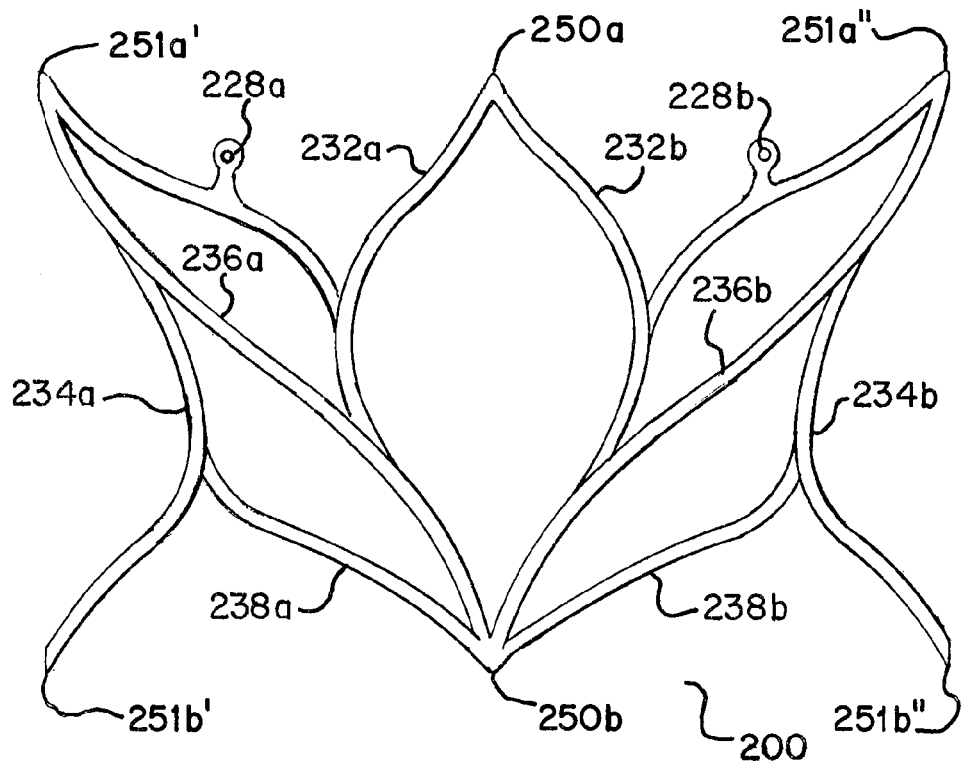
FIG. 5A is a flat plan view of a third support frame.

The transverse connecting members may be formed from the same or different material from one another, and may have the same or different shapes. For example, FIG. 5A shows a flat plan view of a third support frame 200 that is substantially the same as the first support frame 10 in the configuration and orientation of the first member pair 232a, 232b, the second member pair 234a, 234b, and the first pair of transverse connecting members 236a, 236b. However, the second pair of transverse connecting members 238a, 238b and the third pair of transverse connecting members 239a, 239b may be formed from different material than the other portions of the third support frame 200. Alternatively, or in addition, the second pair of transverse connecting members 238a, 238b and the third pair of transverse connecting members 239a, 239b may have a cross sectional area that is different than the other portions of the third support frame 200. For example, the second pair of transverse connecting members 238a, 238b and the third pair of transverse connecting members 239a, 239b may be formed from a biodegradable material and/or may have a larger or smaller cross-sectional area than the other portions of the third support frame 200. Accordingly, the second pair of transverse connecting members 238a, 238b and/or the third pair of transverse connecting members 239a, 239b may be configured to dissipate upon implantation within a body vessel for a desired period of time, or may provide different mechanical properties than other portions of the third support frame 200. Each of the third pair of transverse connecting members 239a, 239b include a radiopaque portion 282a, 282b (respectively) that provide a means for orienting the support frame 200 within a body vessel using fluoroscopy or other imaging means.

Figure 5B:
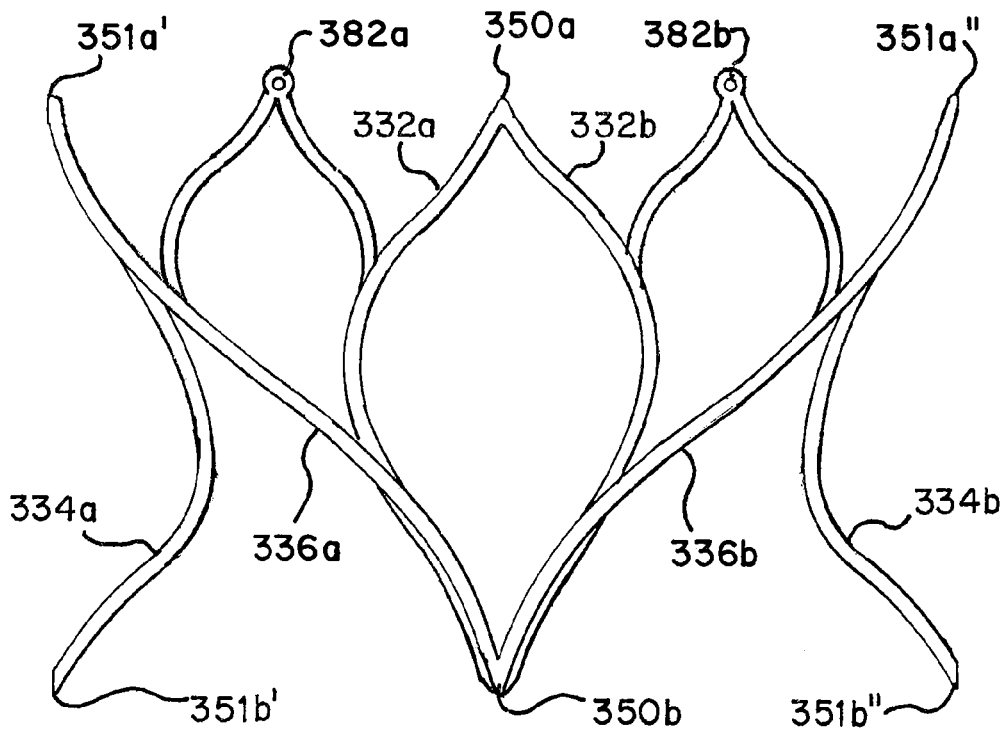
FIG. 5B is a flat plan view of a fourth support frame.

FIG. 5B shows a flat plan view of a fourth support frame 300 that is substantially the same as the first support frame 10 in the configuration and orientation of the first member pair 332a, 332b, the second member pair 334a, 334b, and the first pair of transverse connecting members 336a, 336b. However, the second pair of transverse connecting members 238a, 238b have a different structure than the first pair of transverse connecting members 336a, 336b. In particular, the second pair of transverse connecting members 238a, 238b have a "wishbone" configuration having a radiopaque portion 382a, 382b. In addition, the fourth support frame 300 does not include any transverse connecting members proximal to the first pair of transverse connecting members 336a, 336b.

The support frame may be formed from any suitable material. Preferred materials for support frames include those materials that can provide the desired functional characteristics with respect to mechanical load bearing, biological compatibility, modulus of elasticity, radio-opacity, or other desired properties. For some embodiments, the materials used to form the implantable frames can comprise a material that exhibits excellent corrosion resistance. For some embodiments, the material can be selected to be sufficiently radiopaque and create minimal artifacts during magnetic resonance imaging techniques (MRI). In some embodiments, the implantable frame can comprise a metal, a metal alloy, a polymer, or any suitable combination thereof, for example as frame with multiple layers.

Preferably, the support frames are self-expanding, comprising a material capable of significant recoverable strain to assume a low profile for delivery to a desired location within a body lumen. After release of the compressed self-expanding stent, it is preferred that the frame be capable of radially expanding back to its original diameter or close to its original diameter. Accordingly, some embodiments provide frames made from material with a low yield stress (to make the frame deformable at manageable balloon pressures), high elastic modulus (for minimal recoil), and is work hardened through expansion for high strength. Particularly preferred materials for self-expanding implantable frames are shape memory alloys that exhibit superelastic behavior, i.e., are capable of significant distortion without plastic deformation. Frames manufactured of such materials may be significantly compressed without permanent plastic deformation, i.e., they are compressed such that the maximum strain level in the stent is below the recoverable strain limit of the material. Discussions relating to nickel titanium alloys and other alloys that exhibit behaviors suitable for frames can be found in, e.g., U.S. Pat. No. 5,597,378 (Jervis) and WO 95/31945 (Burmeister et al.). A preferred shape memory alloy is Ni—Ti, although any of the other known shape memory alloys may be used as well. Such other alloys include: Au—Cd, Cu—Zn, In—Ti, Cu—Zn—Al, Ti—Nb, Au—Cu—Zn, Cu—Zn—Sn, CuZn—Si, Cu—Al—Ni, Ag—Cd, Cu—Sn, Cu—Zn—Ga, Ni—Al, Fe—Pt, U—Nb, Ti—Pd—Ni, Fe—Mn—Si, and the like. These alloys may also be doped with small amounts of other elements for various property modifications as may be desired and as is known in the art. Nickel titanium alloys suitable for use in manufacturing implantable frames can be obtained from, e.g., Memory Corp., Brookfield, Conn. One suitable material possessing desirable characteristics for self-expansion is Nitinol, a Nickel-Titanium alloy that can recover elastic deformations of up to 10 percent. This unusually large elastic range is commonly known as superelasticity.

Alternatively, the implantable frames are designed to be expanded by a balloon or some other device (i.e., the frames are not self-expanding), and may be manufactured from an inert, biocompatible material with high corrosion resistance that can be plastically deformed at low-moderate stress levels, such as tantalum. The implantable frames can be deployed by both assisted (mechanical) expansion, i.e. balloon expansion, and self-expansion means. In embodiments where the implantable frame is deployed by mechanical (balloon) expansion, the implantable frame is made from materials that can be plastically deformed through the expansion of a mechanical assist device, such as by the inflation of a catheter based balloon. When the balloon is deflated, the frame can remain substantially in the expanded shape. Other acceptable materials include stainless steel, titanium ASTM F63-83 Grade 1, niobium or high carat gold K 19-22. One widely used material for balloon expandable structures is stainless steel, particularly 316L stainless steel. This material is particularly corrosion resistant with a low carbon content and additions of molybdenum and niobium. Fully annealed, stainless steel is easily deformable. Alternative materials for mechanically expandable structural frames that maintain similar characteristics to stainless steel include tantalum, platinum alloys, niobium alloys, and cobalt alloys.

Optionally, the support frame may be formed from or coated with other materials, such as polymers and bioabsorbable polymers may be included in or on the implantable support frames. The support frames or portions thereof can optionally comprise material that permits identification of the position or orientation of the frame within a body passage. Radiopaque markers are advantageously positioned at one or more ends of the implantable frame to aid the physician in positioning the frame at a site inside a body vessel. For example, portions of the implantable frame can include a radiopaque material that can be identified by X-rays. For example, U.S. Pat. No. 6,409,752, issued Jun. 25, 2002 to Boatman et al., incorporated herein by reference, discloses various radiopaque materials that can be used in or on the implantable frames.

The implantable frames may be fabricated using any suitable method known in the art. Preferably, the complete frame structure is cut from a solid tube or sheet of material, and thus the frame would be considered a monolithic unit. Laser cutting, water-jet cutting and photochemical etching are all methods that can be employed to form the structural frame from sheet and tube stock. Still other methods for fabricating the complete frame structure as previously disclosed would be understood by one of skill in the art.

Alternatively, the frame can also be formed from wire using wire forming techniques, such as coiling, braiding, or knitting. By welding the wire at specific locations a closed-cell structure may be created. This allows for continuous production, i.e. the components of the implantable frame may be cut to length from a long wire mesh tube. In addition, an implantable frame is constructed from sheet, wire (round or flat) or tubing. The method of fabrication can be selected by one skilled in the art depending on the raw material used. Techniques for forming implantable frames are discussed, for example, in Dougal et al., "Stent Design: Implications for Restenosis," Rev. Cardiovasc Med. 3 (suppl. 5), S16-S22 (2002), which is incorporated herein by reference in its entirety.

In some embodiments, connections between the first member pair and/or the second member pair and the transverse connecting members, may be by welding or other suitable connecting means. Other connection means include the use of a binder, heat, or chemical bond, and/or attachment by mechanical means, such as pressing, welding or suturing. In addition, portions of the frame may be attached by applying a bonding coating.

A support frame can optionally be sterilized using any suitable technique known in the art, or equivalents thereto. For example, an implantable frame can be sterilized using ethylene oxide sterilization, as described in AAM/ISO 11 135:1994 "Medical Devices—Validation and Routine Control of Ethylene Oxide Sterilization," incorporated herein by reference in its entirety. In some embodiments, a sterilized implantable frame satisfies a minimum Sterility Assurance Level (SAL) of about $10^{-6}$.

Prosthetic Valve Embodiments

In a second embodiment, prosthetic valve devices are provided. The prosthetic valve preferably includes a support frame described with respect to the first embodiment and a means for regulating fluid through a body vessel. Preferably the prosthetic valve prosthesis devices are configured to treat incompetent or damaged cardiac or venous valves in mammals or to otherwise beneficially modify fluid flow in a bodily passage. For example, a prosthetic valve may be configured to replace or augment the function of natural venous valves operative in veins. The prosthetic venous valve preferably includes a support frame of the first embodiment designed to resist collapsing under the contraction of the muscle present around veins by symmetrically distributing stress and strain within the frame.

Figure 6A:
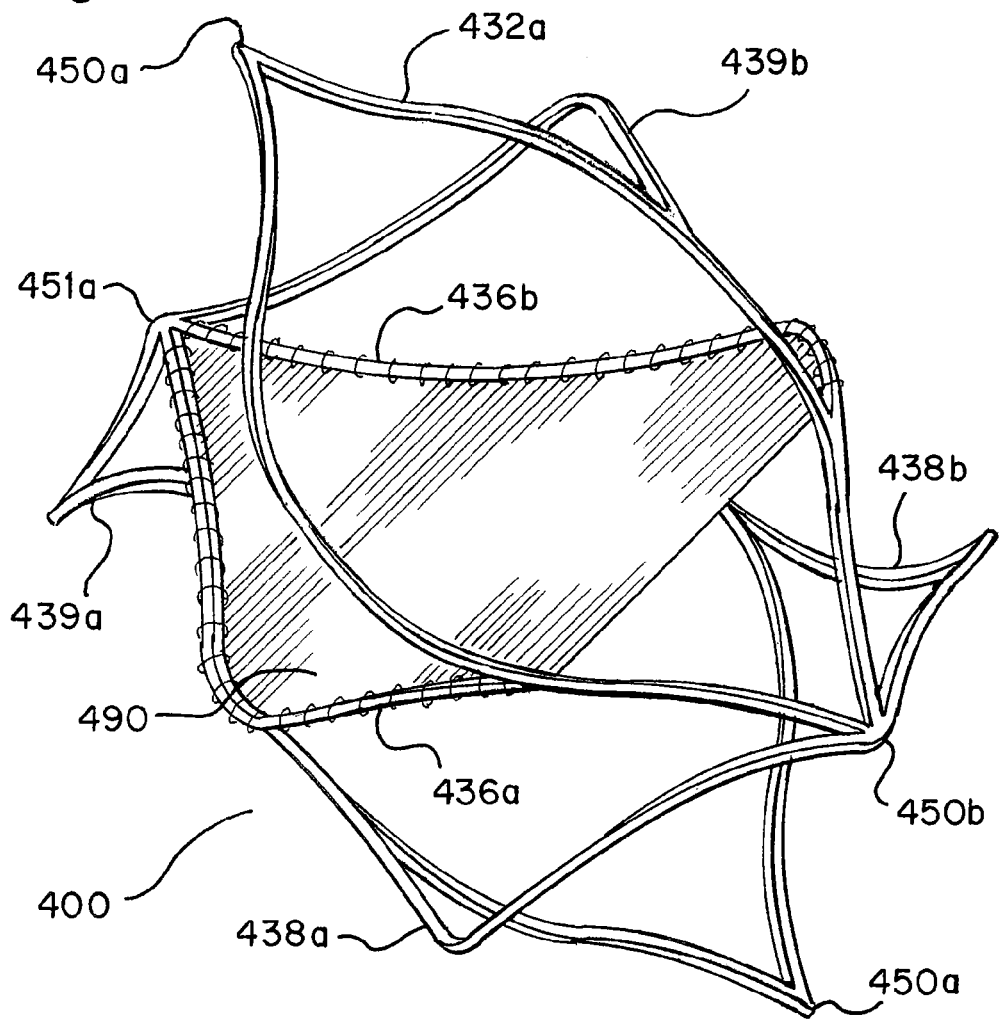
FIG. 6A is a perspective view of a first prosthetic valve including the first support frame.
Figure 6B:
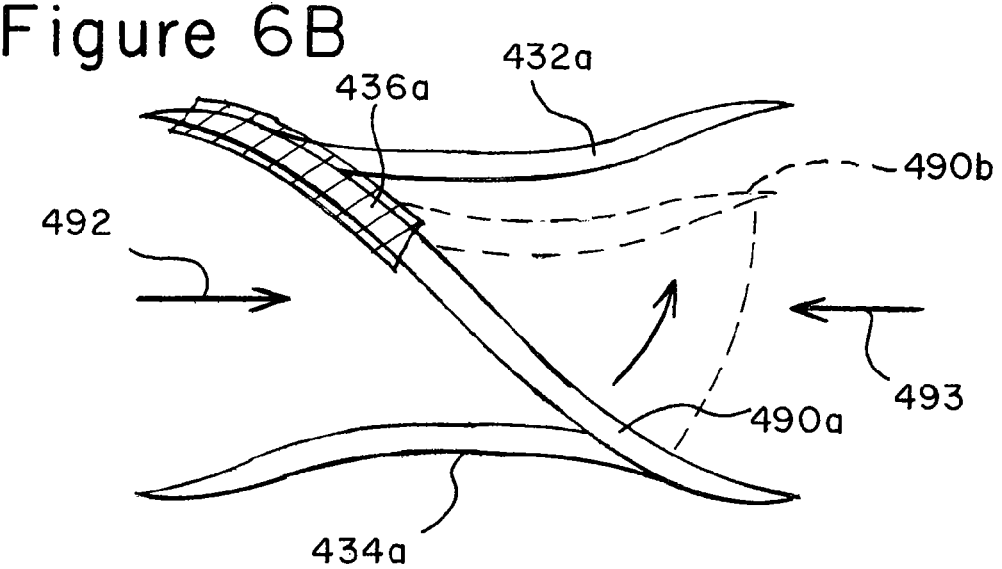
FIG. 6B is a side view of the first prosthetic valve.

One non-limiting example of a suitable prosthetic valve device is shown in FIGS. 6A and 6B, which includes a flexible monocuspid valve member 490 attached to the first support frame 10 described above with respect to FIGS. 1-3. Other prosthetic valves can be formed by attaching a means for regulating fluid flow, such as a valve leaflet or monocuspid valve member, to any support frame described according to the first embodiment. One or more prosthetic valves can be implanted within a tubular body passage of a patient, especially a human, including for example in veins or arteries, to regulate fluid flow therein.

With reference to FIG. 6A, the prosthetic valve 400 includes a support frame 410, which is identical to the frame 10 described above with respect to the first embodiment. A monocuspid valve member 490 is attached to the support frame 410 along the first pair of transverse connecting members 436a, 436b. The monocuspid valve member 490 is configured and attached in a manner to allow a portion of the monocuspid valve member 490 to extend across the lumen of the support frame 410. Preferably, the support frame 410 is radially self-expanding with a maximum diameter that is preferably slightly greater than the body vessel where the prosthetic valve 400 is implanted, such that the support frame 410 exerts sufficient outward radial force against the inner wall of the body vessel to retain the prosthetic valve 400 therein. Alternatively, the support frame may include one or more means to anchor the support frame 410 within a body vessel, such as barbs or adhesives disposed on the outer, vessel-contacting portion of the support frame 410. As shown in FIG. 6A, the valve member 490 may be configured as a single cone or pocket-shaped structure attached to the support frame 410 along the first pair of transverse connecting members 436a, 436b. Preferably, the valve member 490 extends across the lumen of the support frame 410 and contacts the second distal point 451a. The monocuspid valve member 490 can be formed from a suitably flexible material to in response to fluid flow contacting the surface, and can be sized to extend transversely across the lumen of the support frame 410, in a path substantially perpendicular to a longitudinal axis of the support frame 410. The valve member 490 can be a monocuspid structure oriented with the open end of the cone shape facing the direction of longitudinal retrograde 493 fluid flow through lumen.

FIG. 6B shows a side view of the prosthetic valve 400 shown in FIG. 6A operating within a vein to regulate fluid flow. The prosthetic valve 400 is shown with the valve member 490 in an open configuration 490b (dashed line) and a closed configuration 490a (solid line). In the vein, blood flow occurs in a pulsatile fashion, with surges in antegrade fluid flow occurring between intermittent retrograde fluid flow. The prosthetic venous valve 400 preferably provides a one-way valve that permits intermittent blood flow in an antegrade 492 direction while preventing the retrograde 493 fluid flow opposite antegrade direction 492. The monocuspid valve member 490 is a flexible structure configured to moveably traverse the lumen of the support frame 410, and configured to sealably engage the opposite wall of the vein through a portion of the opposite side of the support frame 410. Within the vein as shown in FIG. 6B, the direction of retrograde 493 fluid flow is away from the heart, while antegrade 492 fluid flow proceeds along the longitudinal axis in the direction toward the heart. FIG. 6B depicts the valve member in the open configuration 490b when antegrade blood flow occurs, as blood flow exerts pressure on a first side of the monocuspid valve member 490, urging the leading edge of the valve member 490 back across the lumen of the support frame 410 and forcing out fluid collected in the interior (i.e. "cup") portion 494 of the valve member 490. As the monocuspid valve member 490 opens, the leading edge of a first end is forced away from the vessel wall, opening the prosthetic valve 400 and creating regions around the valve member 490 for unrestricted flow. These regions allow blood to flow in an antegrade direction 492. During retrograde 292 fluid flow, as illustrated in FIG. 6B, blood passes the leading edge along the first end of the valve member 490 causing blood to collect in the interior portion 494 between the valve member 490 and the vein wall. The blood exerts pressure from the retrograde direction 493, urging the leading edge to transversely cross the lumen and sealably engage the vein wall in position 490a. The valve member 490 may have a closed or substantially closed end and an open end in position 490a, allowing the interior portion to quickly fill with the blood flowing in the retrograde direction 493, while preventing blood from flowing through the prosthetic valve 400 in the retrograde direction 493.

Alternatively, a multicusp leaflet configuration may be utilized in the prosthetic valve 400, and the vascular valve device may comprise multiple leaflets configured in such a manner to allow the leaflets to co-apt within the lumen of the support frame 410. The valve leaflets can have any suitable shape. Preferably, the valve leaflet includes one or more edges attached to a valve support frame 410 and extend within the lumen of the support frame 410. The valve leaflets preferably have (n) edges and (n−1) edges of each valve leaflet preferably contact the support frame 410, where (n) is an integer equal to 2 or greater. Valve leaflets with (n) of 2, 3, or 4 are preferred, although leaflets with other shapes can also be used. Preferably, at least two edges of a valve leaflet are attached to a valve support frame 410, and at least one edge of a valve leaflet is a leaflet free edge that is not attached to any support frame.

A wide variety of materials acceptable for use as a monocuspid valve member or valve leaflets are known in the art, and any suitable material can be utilized. The material chosen need only be able to perform as described herein, and be biocompatible, or able to be made biocompatible. Examples of suitable materials include natural materials, and synthetic materials.

In certain embodiments of the invention, the leaflet is formed from a flexible material comprising a naturally derived or synthetic collagenous material, and especially an extracellular collagen matrix material. Examples of suitable natural materials include collagen and extracellular matrix (ECM) material, such as submucosa. The "extracellular matrix" is typically a collagen-rich substance that is found in between cells in animal tissue and serves as a structural element in tissues. Such an extracellular matrix is preferably a complex mixture of polysaccharides and proteins secreted by cells. The extracellular matrix can be isolated and treated in a variety of ways. Following isolation and treatment, it is referred to as an ECM. ECM may be isolated from submucosa (including small intestine submucosa), stomach submucosa, urinary bladder submucosa, tissue mucosa, renal capsule, dura mater, liver basement membrane, pericardium or other tissues. One specific example of ECM is small intestine submucose (SIS). When implanted, SIS can undergo remodeling and can induce the growth of endogenous tissues upon implantation into a host. SIS has been used successfully in vascular grafts, urinary bladder and hernia repair, replacement and repair of tendons and ligaments, and dermal grafts. SIS is particularly well-suited for use as valve members, such as leaflets. Suitable extracellular matrix materials ("ECM material") include, for instance, submucosa (including, for example, small intestinal submucosa ("SIS"), stomach submucosa, urinary bladder submucosa, or uterine submucosa), renal capsule membrane, dura mater, pericardium, serosa, and peritoneum or basement membrane materials, including liver basement membrane. These layers may be isolated and used as intact natural sheet forms, or reconstituted collagen layers including collagen derived from these materials or other collagenous materials may be used. For additional information as to submucosa materials useful in the present invention, and their isolation and treatment, reference can be made to U.S. Pat. Nos. 4,902,508, 5,554,389, 5,993,844, 6,206,931, and 6,099,567, the contents of which are incorporated herein by reference. Renal capsule tissue can also be obtained from warm blooded vertebrates, as described more particularly in copending U.S. patent application Ser. No. 10/186,150, filed Jun. 28, 2002, and International Patent Application Serial Number PCT/US02/20499, filed Jun. 28, 2002, and published Jan. 9, 2003 as International Publication Number WO03002165, the contents of which are incorporated herein by reference. In one embodiment of the invention, the ECM material is porcine SIS. SIS can be prepared according to the method disclosed in U.S. 2004/0180042A1, published Sep. 16, 2004, the contents of which are incorporated herein by reference. In addition to xenogenic biomaterials, such as SIS, autologous tissue can be harvested as well. Additionally Elastin or Elastin Like Polypetides (ELPs) and the like offer potential as a material to fabricate the flexible covering or discrete shaping members to form a device with exceptional biocompatibility. Another alternative is use of allographs such as harvested native valve tissue. Such tissue is commercially available in a cryopreserved state.

In one aspect, the valve member, and preferably a valve leaflet, is formed from explanted biological tissue, such as aortic tissue, that is treated in a manner that improves the biocompatibility of the tissue for an intended use. For example, the tissue may be treated to improve resistance to post-implantation mineralization. One preferred method is described in U.S. Pat. No. 5,595,571 (Filed Apr. 18, 1994), incorporated by reference herein in its entirety, which involves exposing biological material including cellular and non-cellular structural components to a buffered solution having a pH in the range from about 5.0 to about 8.0 and a temperature in the range from about 12° C. to about 30° C. for a sufficient amount of time to facilitate the degradation of cells by autolytic enzymes within the cells, whereby at least one region of the biological material is rendered substantially acellular while preserving the overall structural integrity and non-cellular structural components of the biological material The exposure occurs prior to any fixation of the biological material. Other suitable tissue treatments are described in the following references, all of which are incorporated herein by reference in their entirety: 5,720,777, 5,843,180 and 5,843,181 (Biological Material Pre-fixation Treatment); 4,798,611 (Enhancement of Xenogeneic Tissue by treatment with glutaraldehyde and then irradiation); 4,813,958 (Crosslinked anisotropic mammalian diaphragm in surgical reconstruction); 3,966,401 (Tissue for Implantation so as to Provide Improved Flexibility by Tissue subjecting tissue to tanning fluid when under pressure until the tissue assumes a natural configuration during tanning in Tanning fluids including 4% formaldehyde and 2% glutaraldehyde); 4,800,603 (Tissue Fixation with Vapor by subjecting tissue to a vapor of a fixative while the tissue is unstressed); and 4,813,964 and 4,813,958 (Crosslinked anisotropic xenogenic diaphragm tissue in flexor tendon pulley reconstruction, such as a method of tissue replacement for nonfunctional flexor tendon pulleys including replacing the flexor tendon pulleys with anisotropic, crosslinked mammalian, bovine or porcine diaphragm which is characterized in that the diaphragm has one smooth side and one fibrous side, the smooth side being placed against the flexor tendon). Preferably, the explanted tissue explanted tissue is pre-treated by performing at least one of the following steps: maintaining the explanted tissue at a pH in the range from about 5.0 to about 8.0 and a temperature in the range from about 12° C. to about 30° C. for a sufficient amount of time sufficient to effect the degradation of at least a portion of the cells by autolytic enzymes within the cells; contacting the explanted tissue with a chemical cross-linking agent and then irradiating with X-ray or gamma radiation; contacting the explanted tissue with a tanning fluid including formaldehyde or glutaraldehyde; or placing tissue explanted tissue within an atmosphere of substantially unpressurized vapor of containing glutaraldehyde, and maintaining the tissue within the atmosphere of substantially unpressurized vapor in a manner sufficient to provide substantially uniform application of the fixative solution for a period of time to cause the desired fixation of said tissue.

The valve leaflet may be formed from a synthetic polymeric material. Examples of suitable polymeric materials include polyesters, such as poly(ethylene terephthalate), polylactide, polyglycolide and copolymers thereof; fluorinated polymers, such as polytetrafluroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances.

In addition, the valve leaflet material may be a biocompatible polyurethane or derivative thereof. One example of a biocompatible polyurethane is THORALON (THORATEC, Pleasanton, Calif.), as described in U.S. Patent Application Publication No. 2002/0065552 A1 and U.S. Pat. No. 4,675,361, both of which are incorporated herein by reference. According to these patents, THORALON is a polyurethane base polymer (referred to as BPS-215) blended with a siloxane containing surface modifying additive (referred to as SMA-300). Base polymers containing urea linkages can also be used. The concentration of the surface modifying additive may be in the range of 0.5% to 5% by weight of the base polymer. The SMA-300 component (THORATEC) is a polyurethane comprising polydimethyl siloxane as a soft segment and the reaction product of diphenylmethane diisocyanate (MDI) and 1,4-butanediol as a hard segment. A process for synthesizing SMA-300 is described, for example, in U.S. Pat. Nos. 4,861,830 and 4,675,361, which are incorporated herein by reference. The BPS-215 component (THORATEC) is a segmented polyetherurethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED). THORALON can be manipulated to provide either porous or non-porous THORALON. Porous THORALON can be formed by mixing the polyetherurethane urea (BPS-215), the surface modifying additive (SMA-300) and a particulate substance in a solvent. The particulate may be any of a variety of different particulates or pore forming agents, including inorganic salts that may be removed by contacting the material with a suitable solvent to dissolve and remove the inorganic salt after pore formation. Formation of porous THORALON is described, for example, in U.S. Pat. Nos. 6,752,826 and 2003/0149471 A1, both of which are incorporated herein by reference. Non-porous THORALON can be formed by mixing the polyetherurethane urea (BPS-215) and the surface modifying additive (SMA-300) in a suitable solvent, such as dimethyacetamide (DMAC). The composition can contain from about 5 wt % to about 40 wt % polymer, and different levels of polymer within the range can be used to fine tune the viscosity needed for a given process. The composition can contain less than 5 wt % polymer for some spray application embodiments. The entire composition can be cast as a sheet, or coated onto an article such as a mandrel or a mold to form a valve leaflet, which can be dried to remove the solvent.

The monocuspid valve member 220 or two or more valve leaflets may be securely mounted to the support frame 210 by any suitable means. The valve leaflet material can be attached to the support frame by any appropriate attachment means, including but not limited to, adhesive, fasteners, and tissue welding using heat and/or pressure. Alternatively, the valve leaflet may be formed on the support frame by an appropriate means, including but not limited to vapor deposition, spraying, electrostatic deposition, ultrasonic deposition, or dipping. One or more valve leaflets can be attached to the support frame by other methods. In one embodiment, a sheet of material is cut to form a valve leaflet and the edges of the leaflet are wrapped around portions of a support frame and portions of the valve leaflet sealably connected together to fasten the valve leaflet around the support frame. For example, one edge of a sheet of valve leaflet material can be wrapped around a portion of the support frame and held against the body of the valve leaflet, so that the valve leaflet material forms a lumen enclosing a portion of the support frame. A small amount of a suitable solvent is then applied to the edge of the valve leaflet material to dissolve the edge into an adjacent portion of the valve leaflet material and thereby seal the material around the support frame.

In another embodiment, the sheet of valve leaflet material is shaped to form the valve leaflet that is attached to a portion of a support frame using stitching through the valve leaflet material and around a portion of the support structure, adhesives, tissue welding or cross linking to directly join the valve leaflet material to the support frame. A valve leaflet attached to a support frame can be permitted to move relative to the support frame, or the valve leaflet can be substantially fixed in its position or orientation with respect to the support frame by using attachment configurations that resist relative movement of the valve leaflet and the support frame.

Methods of Delivery and Treatment

Artificial valve prostheses can be deployed at various locations and lumens in the body, such as, for example, coronary, vascular, nonvascular and peripheral vessels, ducts, and the like. In one embodiment, a valve leaflet is attached to the support frame to provide an implantable valve prosthesis that can be implanted within a vein, for instance, near an incompetent venous valve to treat venous valve insufficiency. Prosthetic valve devices of the present invention are desirably adapted for deployment within the vascular system, and in certain preferred embodiments, are adapted for deployment within the venous system. Accordingly, a prosthetic valve can be adapted as a venous valve, for example, for attachment within veins of the legs or feet, to treat venous insufficiency.

The prosthetic valves described herein can be configured for delivery to a body vessel in a radially compressed configuration, and radially expanded at a point of treatment within the body vessel. The overall configuration, cross-sectional area, and length of a medical device frame having a tubular configuration (compressed or expanded) may depend on several factors, including the size and configuration of device, the size and configuration of the vessel in which the device will be implanted, the extent of contact between the device and the walls of the vessel, and the amount of retrograde flow through the vessel that is desired.

Preferably, the support frames and/or prosthetic valves described above can be radially intraluminally delivered inside the body by a catheter that supports the implantable frame in a compacted form as it is transported to the desired site, for example within a body vessel. Upon reaching the site, the implantable support frame can be expanded and securely placed within the body vessel, for example by securely engaging the walls of the body vessel lumen. The expansion mechanism may involve permitting the support frame to expand radially outward, for example, by inflation of a balloon formed in the distal portion of the catheter, to inelastically deform the stent and fix it at a predetermined expanded position in contact with the lumen wall. The expansion balloon can then be deflated and the catheter removed. In another technique, the implantable support frame is formed of a material that will self-expand after being compacted. During introduction into the body, the implantable support frame is restrained in the compacted condition. When the stent has been delivered to the desired site for implantation, the restraint is removed, allowing the implantable frame to self-expand by its own internal elastic restoring force. Once the implantable frame is located at the constricted portion of the lumen, the sheath is removed to expose the stent, which is expanded so it contacts the lumen wall. The catheter is subsequently removed from the body by pulling it in the proximal direction, through the larger lumen diameter created by the expanded prosthesis, which is left in the body.

Implantable support frames or prostheses comprising the implantable support frame can be delivered into a body lumen using a system which includes a catheter. An appropriately sized delivery catheter can be selected by one skilled in the art for a given application. For example, some embodiments can be delivered using a delivery catheter selected from one or more delivery catheter sizes from the group consisting of: 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 French (F) delivery catheters, or increments of 0.1 F therebetween. In some embodiments, a delivery catheter sized between 1 and 25 F, or preferably between about 1.5 F and 5 F can be used, preferably a 1.8 F (0.60 mm), 2.0 F (0.66 mm), 2.3 F (0.75 mm), 2.6 F (0.85 mm), 2.7 F (0.9 mm), 2.9 F (0.95 mm), or 3.3 (1.10 mm) delivery catheters.

The implantable support frames and/or prosthetic valves can be placed in any medically appropriate location for a given application. For example, in some embodiments, the implantable support frame can serve as part of a venous valve prosthetic and be implanted in the femoral vein, including at the proximal (groin), mid (mid section) or distal (adjacent to the knee) portions of the vein. Preferably, prosthetic valves are placed in the superficial venous system, such as the saphenous veins in the leg, or in the deep venous system, such as the femoral and popliteal veins extending along the back of the knee to the groin.

Methods of treatment preferably include the steps of loading a prosthetic valve in a radially compressed configuration into a delivery catheter, inserting the delivery catheter into a body vessel, translating the delivery catheter to a treatment site, deploying the artificial valve prosthesis by placing the artificial valve prosthesis in an expanded configuration at the treatment site to treat the subject, and withdrawing the delivery catheter from the body vessel.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention. It is therefore intended that the foregoing detailed description be regarded as illustrative rather than limiting, and that it be understood that it is the following claims, including all equivalents, that are intended to define the spirit and scope of this invention.

What is claimed is:

1. A radially-expandable implantable medical device having a support frame moveable from a radially expanded configuration to a radially compressed configuration, the support frame in the expanded configuration defining a lumen extending from a proximal end to a distal end along a longitudinal axis and defining a plurality of openings in communication with the lumen, the support frame comprising:
   a first member pair of circumferentially adjacent members joined at a first distal point positioned at the distal end of the support frame and at a first proximal point positioned at the proximal end of the support frame, each member of the first pair having a divergent portion joined to a convergent portion at an inflection point, with the divergent portion extending circumferentially away from the proximal point and toward the inflection point and the convergent portion extending circumferentially away from the inflection point and toward the distal point, the first member pair of circumferentially adjacent members defining a first opening in the support frame;
   a second member pair of circumferentially adjacent members joined at a second distal point positioned at the distal end of the support frame and at a second proximal point positioned at the proximal end of the support frame, each member of the second member pair having a divergent portion joined to a convergent portion at an inflection point, with the divergent portion extending circumferentially away from the distal point and toward the inflection point and the convergent portion extending circumferentially away from the inflection point and toward the proximal point, the second member pair of circumferentially adjacent members defining a second opening in the support frame;
   the first member pair connected to the second member pair by a first pair of transverse connecting members and a second pair of transverse connecting members, each transverse connecting member of the first pair of transverse connecting members extending from the divergent portion of one member of the first member pair to a divergent portion of one member of the second member pair and each transverse connecting member of the second pair of transverse connecting members extending from either the divergent portion of one member of the first member pair to a convergent portion of one member of the second member pair or from the convergent portion of one member of the first member pair to a divergent portion of one member of the second member pair;
   the first opening being opposably positioned across the lumen with respect to the second opening.

2. The medical device of claim 1, wherein the first opening has four sides.

3. The medical device of claim 1, wherein the second opening has four sides.

4. The medical device of claim 3, wherein the first opening is congruent to the second opening.

5. The medical device of claim 4, where the first opening and the second opening each have a petal-like shape or a diamond-like shape.

6. The medical device of claim 1, wherein the support frame further comprises one or more additional transverse connecting members extending between the first member pair and the second member pair.

7. The medical device of claim 1, wherein the first member pair, the second member pair and the first pair of transverse connecting members have a substantially uniform first cross-sectional area.

8. The medical device of claim 7, wherein the support frame further comprises one or more additional transverse connecting members extending between the first member pair and the second member pair, the additional transverse connecting members having a substantially uniform second cross-sectional area that is different from the first cross-sectional area.

9. The medical device of claim 8, wherein the additional transverse connecting members comprise a biodegradable material.

10. The medical device of claim 9, wherein the first member pair, the second member pair and the first pair of transverse connecting members comprise a biocompatible metal.

11. The medical device of claim 1, wherein the first member pair, the second member pair and the first pair of transverse connecting members comprise a shape-memory alloy.

12. A radially-expandable implantable prosthetic valve moveable from a radially expanded configuration to a radially compressed configuration, the prosthetic valve in the expanded configuration defining a lumen extending from a proximal end to a distal end along a longitudinal axis and defining a plurality of openings in communication with the lumen, the prosthetic valve comprising:
   (a) a support frame including a first member pair defining a first opening connected to a second member pair defining a second opening by a pair of curvilinear transverse connecting members,
   the first member pair comprising a first pair of circumferentially adjacent members joined at a first distal point positioned at the distal end of the support frame and at a first proximal point positioned at the proximal end of the support frame, each member of the first member pair having a divergent portion joined to a convergent portion at a first inflection point, with the divergent portion extending circumferentially away from the proximal point and toward the first inflection point and the convergent portion extending circumferentially away from the first inflection point and toward the distal point, the first pair of circumferentially adjacent members defining a first opening in the support frame having a diamond-like or petal-like shape;
   the second member pair comprising a second pair of circumferentially adjacent members joined at a second distal point positioned at the distal end of the support frame and at a second proximal point positioned at the proximal end of the support frame, the second member pair being substantially congruent to the first member pair with each member of the second member pair having a divergent portion joined to a convergent portion at a second inflection point, the divergent portion extending circumferentially away from the distal point and toward the second inflection point and the convergent portion extending circumferentially away from the inflection point and toward the proximal point, the second pair of circumferentially adjacent members defining a second opening in the support frame, the first distal point and the first proximal point each being opposably positioned across the lumen with respect to the second distal point or the second proximal point, respectively;
   the first member pair connected to the second member pair by a first pair of curvilinear transverse connecting members and a second pair of curvilinear transverse connecting members, each curvilinear transverse connecting member of the first pair of curvilinear transverse connecting members extending from the divergent portion of one member of the first member pair to a divergent portion of one member of the second member pair and having a third inflection point therebetween, and each transverse connecting member of the second pair of transverse connecting members extending from either the divergent portion of one member of the first member pair to a convergent portion of one member of the second member pair or from the convergent portion of one member of the first member pair to a divergent portion of one member of the second member pair; the first opening being substantially congruent and opposably positioned across the lumen with respect to the second opening; and (b) a means for regulating fluid flow through the lumen attached to the support frame.

13. The prosthetic valve of claim 12, wherein the means for regulating fluid flow is a valve leaflet attached to the support frame and moveable within the lumen to regulate fluid flow therein.

14. The prosthetic valve of claim 13, wherein the means for regulating fluid flow is a valve leaflet comprising a first edge attached to a first curvilinear transverse connecting member of the support frame and a second edge attached to a first curvilinear transverse connecting member of the support frame, the valve leaflet being positioned within the lumen, wherein the valve leaflet prevents or permits fluid flow through the lumen.

15. The artificial valve prosthesis of claim 13, wherein the valve leaflet comprises a material of small intestine submucosa.

16. The medical device of claim 12, wherein the support frame further comprises one or more additional transverse connecting members extending between the first member pair and the second member pair.

17. The medical device of claim 12, wherein the first member pair, the second member pair and the first pair of transverse connecting members have a substantially uniform first cross-sectional area.

18. The medical device of claim 17, wherein the support frame further comprises one or more additional transverse connecting members extending between the first member pair and the second member pair, the additional transverse connecting members having a substantially uniform second cross-sectional area that is different from the first cross-sectional area.

19. The medical device of claim 18, wherein the first member pair, the second member pair and the first pair of transverse connecting members comprise a shape-memory metal.

* * * * *